United States Patent
Powers

(10) Patent No.: US 6,768,038 B2
(45) Date of Patent: Jul. 27, 2004

(54) ALPHA OLEFIN PRODUCTION

(75) Inventor: Donald H. Powers, Pearland, TX (US)

(73) Assignee: Equistar Chemicals, LP, Houston, TX (US)

( * ) Notice: Subject to any disclaimer, the term of this patent is extended or adjusted under 35 U.S.C. 154(b) by 0 days.

(21) Appl. No.: 10/324,450

(22) Filed: Dec. 20, 2002

(65) Prior Publication Data
US 2004/0122278 A1 Jun. 24, 2004

(51) Int. Cl.$^7$ .............................. C07C 5/22; C07C 5/23; C07C 5/25
(52) U.S. Cl. ...................... 585/664; 585/665; 585/666; 585/667; 585/668; 585/669
(58) Field of Search ................. 585/664, 665, 585/666, 667, 668, 669

(56) References Cited

U.S. PATENT DOCUMENTS

| | | | |
|---|---|---|---|
| 2,943,125 A | 6/1960 | Ziegler et al. | 260/683.15 |
| 3,326,865 A | 6/1967 | Haag | 260/79.3 |
| 3,475,511 A | * 10/1969 | Manning | 585/324 |
| 3,962,367 A | 6/1976 | Germanas et al. | 260/683.2 |
| 4,232,177 A | 11/1980 | Smith, Jr. | 585/324 |
| 4,242,530 A | 12/1980 | Smith, Jr. | 585/510 |
| 4,435,606 A | 3/1984 | Motz et al. | 585/324 |
| 4,510,336 A | 4/1985 | Hearn | 568/697 |
| 4,692,430 A | 9/1987 | Welch | 502/342 |
| 4,935,577 A | 6/1990 | Huss, Jr. et al. | 585/726 |
| 4,962,267 A | 10/1990 | Slaugh | 585/670 |
| 4,992,612 A | 2/1991 | Suzukamo et al. | 585/664 |
| 4,992,613 A | 2/1991 | Brownscombe | 585/666 |
| 5,087,780 A | * 2/1992 | Arganbright | 585/259 |
| 6,495,732 B1 | 12/2002 | Hearn et al. | 585/664 |

* cited by examiner

Primary Examiner—Thuan D Dang
(74) Attorney, Agent, or Firm—Roderick W. MacDonald

(57) ABSTRACT

A method for making alpha olefins from internal olefins using catalytic distillation techniques and an olefin double bond isomerization catalyst, and separately recovering said alpha olefins.

5 Claims, No Drawings

ALPHA OLEFIN PRODUCTION

BACKGROUND OF THE INVENTION

This invention relates to the preferential formation of and efficient recovery of alpha olefins by the employment of catalytic distillation in combination with olefin double bond isomerization (shifting of double bonds within an olefin molecule between internal double bonds and double bonds in the alpha position).

DESCRIPTION OF THE PRIOR ART

Heretofore higher olefins (4 carbon atoms per molecule and higher) have been formed by way of lower olefin (2 or 3 carbon atoms per molecule) oligomerization, see U.S. Pat. No. 2,943,125 to Ziegler et al.

Also heretofore alpha olefins (hereinafter a-olefins) have been oligomerized by using catalytic distillation, see U.S. Pat. No. 4,935,577 to Huss, Jr., et al.

Further heretofore the α-olefin 3-methyl butene-1 (hereinafter 3MB1) has been formed by dehydration of isoamyl alcohol using base treated alumina.

Finally, U.S. Pat. No. 4,435,606 to Motz et al. heretofore taught the formation of olefins using aluminum alkyls and then transformation of the α-olefins present, in part to internal olefins (olefin molecules with internal double bonds as opposed to olefin molecules with double bonds in the alpha position) using a conventional isomerization reaction. Motz et al. disclose that a conventional isomerization reaction carried out in a conventional isomerization reactor "randomizes the double bond placement such that only about 2% alpha olefins remain." This is due to the chemical equilibrium constraints that exist at conditions that are present in a conventional isomerization reactor. By "equilibrium constraints" what is meant is the balance between α-olefins and internal olefins that a given isomerization reaction cannot exceed due to thermodynamic chemical equilibrium. In the case of the illustration of Motz et al. their conventional isomerization reaction reaches equilibrium of 2% α-olefins, the remaining olefins in the conventional reactor being internal olefins, and maintains that relative equilibrium between α-olefins and internal olefins throughout that conventional isomerization reaction. Thus, the amount of α-olefins formed in the Motz et al. illustration is limited by reaction equilibrium constraints to 2% α-olefins with the remainder of the olefins in the product being internal olefins.

SUMMARY OF THE INVENTION

In accordance with this invention α-olefins are continuously formed using conventional isomerization catalyst and then promptly and efficiently removed from the reaction by employing that catalyst in a catalytic distillation column (tower).

By the method of this invention, the isomerization catalyst is employed in a distillation tower in known manner so that the α-olefins are formed under distillation conditions that favor speedy removal of the just formed α-olefins out of the isomerization reaction and out of the tower.

This overcomes the equilibrium constraints of the isomerization reaction as described hereinabove without eliminating the function thereof, and continuously drives the isomerization reaction toward the formation of ever more α-olefins.

Thus, by this invention, α-olefins are continually formed in a distillation tower, are promptly removed from the isomerization reaction locale in that tower (reactor) by the distillation conditions under which they were formed, and are just as promptly removed from that reactor and tower for efficient collection of same for further use. This invention thus makes use of the natural equilibrium drive of the isomerization reaction to continuously make α-olefins by the continuous swift and efficient removal of α-olefins from the distillation tower, the reaction never reaches, much less maintains, its natural equilibrium constraint between α-olefins and internal olefins. This allows the overall conversion of internal olefins to far exceed that possible in a conventional isomerization reactor.

DETAILED DESCRIPTION OF THE INVENTION

By this invention α-olefins are formed by catalytic distillation techniques using (A) an olefin double bond isomerization reaction that will produce either a net amount of either α-olefins or internal olefins depending on the relative ratios of these compounds in the reaction zone so long as the isomerization reaction has a natural reaction equilibrium point at which a relative mixture of α-olefins and internal olefins are produced and maintained during the normal course of the isomerization reaction process, and (B) distillation conditions within the catalytic distillation tower that favor (1) the isomerization reaction in the area or areas of the tower where the isomerization catalyst is located and (2) the prompt removal of α-olefins from the distillation tower, preferably the top end of the tower together with refluxing of internal olefins down within the distillation tower giving them the opportunity to react to form α-olefins in the catalyst section.

As noted hereinabove with the Huss, Jr., et al. patent it is well known in the art to process olefins using catalytic distillation. Basically, in this process a distillation (fractionation) column (tower) and a catalytic reactor are combined in a single vessel. Catalyst is fitted into a conventional fractionation tower equipped with an overhead condenser, reflux pump, reboiler, internal stages such as fractionation trays, and standard control instrumentation. Depending on the boiling point range of the specific feed being employed, which can vary widely, the feed is introduced into the interior of the tower, in the vicinity of the catalyst so that at least the component(s) of the feed that is to be isomerized in the presence of the catalyst travels into contact with the catalyst. Preferably, the feed is introduced so that the higher boiling point internal olefins are refluxed down into the catalyst from an upper section of the tower into the catalyst zone and so that these internal olefins are boiled up from a lower section of the tower up into the catalyst zone. Thus, depending on the feed composition, the feed can be introduced above or below a given catalyst bed depending on the ratio of the reactants in the feed and the desired products.

The distillation conditions in the tower can vary widely depending on the feed composition, catalyst isomerization function, desired separation of feed components within the tower, and the like, but generally a temperature and pressure gradient will be established within the tower so that the reaction conditions required by the isomerization reaction are established in the tower in the area where the catalyst bed or beds are located and the distillation conditions throughout the interior of the tower favor removal of the desired α-olefin promptly and continuously to one end of the tower and movement of the remainder of the feed, or at least internal olefins, to the opposite end of the tower. The distillation conditions can also govern where the catalyst bed(s) is located within tower, i.e., in a central location between the tower top and bottom, or closer to the top or the bottom.

The catalyst employed in the tower must be stable and insoluble in the feed and reaction product, and should be relatively immune to poisoning to minimize replacement costs. The catalyst itself can be a solid material contained in packets stitched into fiberglass cloth which cloth is rolled into bundles with alternate layers of wire mesh. In operation, fluids moving within the tower, either upwardly or downwardly, flow freely into and out of the bundles, providing a constant exchange over the catalyst surface. Multiple bundles of varying diameters can be used to cover the cross section of the tower, and each layer of bundles can be staggered to minimize fluid by-passing. The total bed height of a specific catalyst bed in a tower (reactor and reaction zone) and its relative location within the tower is determined by a number of variables well known in the art such as the feed composition, catalyst composition, possible distillation conditions, desired product composition and purity, desired component separation within the tower, and the like. The desired isomerization reaction occurs with the various feed components in a fluid (gas and/or liquid) state in physical contact with the catalyst.

Catalytic distillation is widely used and well known in the art. In addition to α-olefin oligomerization, it has been either commercially used or fully and completely disclosed for use for producing MTBE (U.S. Pat. No. 4,232,177), producing cumene, separating isobutene from a mixture of isobutene and n-butene (U.S. Pat. No. 4,242,530), transetherification (U.S. Pat. No. 4,510,336), and aromatic alkylation. Catalytic distillation is so well known in the art further detail is not required to inform the art.

The advantages of this invention are numerous and not altogether obvious.

First, although it would be preferred that a catalyst be employed that forms more α-olefins than internal olefins for obvious reasons, what is not so obvious is that since there is presently no such catalyst available for the double bond isomerization reaction, this invention can employ a catalyst that would form more internal olefins than α-olefins in a conventional isomerization process even though the desired product of this invention is α-olefins. This is so because by operating under distillation conditions which efficiently remove α-olefins from the catalytic reaction zone, the isomerization reaction never reaches its natural equilibrium point between the relative concentrations of α-olefins and internal olefins present in the reaction. Thus, whatever type of isomerization catalyst is present in the tower reaction zone (the isomerization reactor), the catalyst is, by this invention's constant removal of α-olefin from the reaction zone, constantly driven to make more α-olefin to reach its natural equilibrium point between α-olefin and internal olefin. Thus, this invention is unexpectedly robust in the very wide variety of isomerization catalysts useful therein, even when such catalysts do not favor the formation of the desired α-olefin product.

This invention also has the unobvious advantage that less stages of separation by distillation are required to achieve the desired separation of α-olefin from internal olefin. As is well known in the art a separation of a 50/50 mix of α-olefin and internal olefin requires a very large number of theoretical separation (distillation) stages, e.g., distillation tower trays. By the combination of the isomerization reaction under distillation conditions, this invention can obtain a desired purity of α-olefin product with a lesser number of separation stages.

This invention is especially useful for byproduct streams that are normally used for the production of fuels because it enables the low value olefins to be converted into α-olefin products, such as butene-1, 3MB1 defined hereinabove, pentene-1, and hextene-1, which α-olefins can then be used to make other valuable products. For example, α-olefins can be employed as a comonomer in the formation of polyethylene to yield a branched chain polymer product that is less brittle and has better impact strength than linear (unbranched) polyethylene.

Because of the elimination of normal equilibrium constraints as aforesaid, this invention can be employed to great advantage on low value, low concentration mixed olefin byproduct streams to form additional α-olefins and efficiently recover the newly formed a-olefins. Examples of such byproduct streams are mixed 5 carbon atom per molecule ($C_5$) hydrocarbon streams from a refinery or olefin plant that contain internal olefins in even minor amounts, and ethylene metathesis byproduct streams. Ethylene dimerization streams and Fischer-Tropsch product streams are particularly well suited for the production of linear α-olefins. However, any other hydrocarbon stream that has a significant internal olefin content can be used. Thus, by this invention, low value by product streams containing olefins, whether alpha, internal, or mixtures thereof, become a more valuable feed source for α-olefins.

This invention is especially valuable for processing hydrocarbon streams containing branched chain mixed methyl butenes since it will convert 2-methyl butene-1 (2MB1) and/or 2-methyl butene-2 (2MB2) to 3MB1. When recovered from the tower, the 3MB1 stream can be used to make other products, e.g., 3MB1 can be used as a monomer for polymer production or as a comonomer for making branched chain polyethylene. The 3MB1 product is especially suited to the application of this invention since it has a boiling point that is significantly lower than the other $C_5$ product's molecules.

A last, but certainly not least, advantage for this invention is in the upgrading of the automotive gasoline pool. $C_5$ olefins are known as a volatile organic compound that contributes disproportionately to air pollution. The 3MB1 compound has significantly lower boiling point than other $C_5$ compounds normally found in hydrocarbon streams that are employed in the gasoline pool of hydrocarbon streams from which automotive gasoline for the motoring public is prepared. By preferentially and directionally forming and removing 3MB1, this invention provides for the easy and ready removal of $C_5$ olefins that can be converted into 3MB1 from those hydrocarbon streams and, therefore, from the gasoline pool.

Put another way, by this invention a $C_5$ containing stream, in which at least some of the $C_5$'s are olefins, can be efficiently depleted in its $C_5$ olefin content before being added to the gasoline pool by directionally driving the conversion of internal $C_5$ olefins to newly formed 3MB1 which is then promptly removed from the host stream by the catalytic distillation conditions present as the 3MB1 is formed.

The feed to the catalytic distillation tower can vary widely, but preferably contains olefins (internal or mixture of internal and alpha) having from 4 to 12 carbon atoms per molecule ($C_4$ to $C_{12}$), inclusive, still more preferably $C_5$ to $C_{10}$, inclusive. The olefin content of the feed should have at least a significant content of internal olefins that can be converted to α-olefins with the appropriate catalyst and isomerization conditions, preferably at least about 5 weight percent internal olefins based on the total weight of the feed, still more preferably at least about 30 weight percent internal olefins based on the total weight of the feed. The feed, depending on its content and the isomerization reaction and distillation conditions, will be introduced above or below the catalyst bed reaction zone. Preferably at present, the feed is introduced so that the internal olefins are refluxed down into the reaction zone from an upper section of the tower and reboiled up into the reaction zone from a lower section of the tower, and α-olefins rise out of the reaction zone toward the top of the tower while internal olefins travel downwardly toward the bottom of the tower. Suitable feed streams for this invention can be light olefin product streams from a Fischer-Tropsch reactor, steam cracker, catalytic cracker and the like. Product streams containing $C_5$ olefins are especially useful.

The isomerization catalyst used in this invention can vary widely especially since this invention can employ to advantage catalysts that favor the formation of internal olefins over α-olefins. Generally, the catalysts employed promote double bond shifts within a specific olefin molecule (double bond isomerization), so any such catalyst that is suitable for use in a catalytic distillation process can be used. The catalysts useful in this invention will be obvious to one skilled in the art since they are either commercially available or fully and completely disclosed in the prior art. Such catalysts include acidic ion exchange resins such as sulfonated resins with sulfonic acid sites (U.S. Pat. No. 3,326,866), perfluorinated polymer sulfonic acid catalyst, phosphoric acid catalyst, carboxylic acid catalyst, fluorinated alkyl sulfonic acid catalyst, alumina plus alkali metal (U.S. Pat. No. 4,992,612), zinc aluminate (U.S. Pat. No. 4,692,430), zirconia, sulfated zirconia, cobalt/sulfur catalyst (U.S. Pat. No. 3,962,367), ruthenium oxide (U.S. Pat. No. 4,962,267), alumino phosphates, and zeolite structures with or without alkali metal (U.S. Pat. No. 4,992,613).

The isomerization conditions useful in this invention will be obvious to one skilled in the art once apprised of this invention, but will generally be temperature and pressure conditions suitable to cause double bond isomerizations in an olefin molecule whether from the alpha position to an internal position or vice versa. The temperature range within the portion of the tower that encompasses the locale of the catalyst will generally be from about 0° to about 500° C., preferably from about 0° to about 200° C. Some catalysts will require higher isomerization temperatures than others. Also, the isomerization operating range of a catalyst is best at or about (plus or minus 10° C.) the boiling point of the specific feed to that catalyst at the operating pressure of the distillation column. The isomerization pressure range will vary widely given the wide range of feeds and catalysts useful, but will work in conjunction with the temperature range aforesaid to provide the desired isomerization reaction, and will generally be from about 0 psig to about 250 psig.

The distillation conditions within the tower will be broader than the aforesaid isomerization conditions but will encompass the isomerization conditions so that at least one catalyst bed can be fixed in the interior of the tower in a temperature and pressure environment that meets the isomerization reaction temperature and pressure requisites for that particular catalyst bed. Thus, the catalyst could be located anywhere along the internal height of the tower where the desired isomerization conditions are present. A given catalyst could be located centrally of the height of the tower, or nearer the top of the tower, or nearer the bottom of the tower depending on where in the tower the combination of temperature and pressure conditions best match the necessary isomerization conditions and product purity requirements. The tower temperature range from tower bottom to tower top will vary widely depending upon the boiling characteristics of the feed material, particularly its boiling range. Generally, the broader the boiling range of the feed, the broader the temperature range for the tower, and an increase in pressure in the tower provides a higher temperature in the tower for the isomerization reaction. It is presently preferred that the distillation conditions of temperature and pressure encompass the isomerization conditions of temperature and pressure so that the catalyst can be situated in the tower along the height thereof in a manner such that the feed can be introduced into the tower above the catalyst and the α-olefins already in the feed migrate upwardly, due to the distillation conditions at the point of feed entry, to the top of the tower for removal while the internal olefins migrate downwardly to the catalyst and toward the bottom of the tower, the remainder of the feed components moving up or down in the tower as is natural for the individual components in the feed under the given distillation conditions.

In the process of this invention, depending on the feed composition, reaction conditions, distillation conditions, specific catalyst employed, and the like, a substantial amount of internal olefin in the feed is converted to α-olefin product. This internal olefin conversion amount can be at least about 30 weight percent, based on the total weight of the feed, and in some cases can approach as high as 90 weight percent conversion to α-olefin product.

Heavy, unreactive components present in the feedstock along with any internal olefins that are ultimately not converted to α-olefins are removed from the tower, preferably as tower bottoms product, for subsequent processing.

EXAMPLE 1

A stream produced by ethylene dimerization containing 88 weight percent, based on the total weight of the feed, of a mixture of cis-butene-2 and transbutene-2 is employed as a feed to a conventional catalytic distillation tower containing an olefin double bond isomerization catalyst comprising sulfonated resin with sulfonic acid sites (see U.S. Pat. No. 3,326,866) in a generally central location along the interior height of the tower. The feed is introduced into the tower above the catalyst and falls downwardly into contact with the catalyst whereby at least about 50 weight percent based on the total weight of the feed of the cis-butene-2 and transbutene-2 mixture in the feed is transformed into 1-butene.

The temperature range within the tower is from 90° C. at the tower bottom to 75° C. at the tower top, and the tower is essentially at 180 psig at the bottom and 160 psig at the top. This establishes the distillation conditions within the tower.

The catalyst is located within the tower at a location where the prevailing temperature is in the range of from about 80° C. to about 90° C. which is the required temperature range for efficient operation of the isomerization reaction of cis-butene-2 and transbutene-2 to 1-butene using the aforesaid catalyst.

1-butene formed in the isomerizaiton reaction zone of the tower that contains the catalyst rises promptly upwardly out of the reaction zone to the top of the tower where it is removed as tower overhead and collected for further use. The remainder of the feed, including untransformed cis-butene-2 and transbutene-2 is refluxed downward to the reaction section of the tower. Unreacted cis-butene-2 and transbutene-2 that exit the reaction section at the bottom of the tower are reboiled up into the reaction section from the reboiler of the column. This provides multiple opportunities for double bond conversion of the internal olefins as they pass through the reaction zone. Unreactive components present in the feedstock along with any internal olefins that are ultimately not converted are removed in the tower bottoms product for subsequent processing.

EXAMPLE 2

A raffinate stream from a steam (thermal) cracker containing 8 weight percent, based on the total weight of the feed, of a mixture of 2MB1 and 2MB2 is employed as a feed to a conventional catalytic distillation tower that contains in a generally central section of the tower an olefin double bond isomerization catalyst comprising sulfonated resin with sulfonic acid sites (see U.S. Pat. No. 3,326,866).

The feed is introduced into the tower above the catalyst and falls downwardly into contact with the catalyst wherein at least about 30 weight percent, based on the total weight of the feed, of the mixture of 2MB1 and 2MB2 is transformed into 3MB1.

The temperature range within the tower is from about 96° C. at the tower bottom to about 60° C. at the tower top, and the tower is essentially at 40 psig at the bottom and 20 psig at the top. This establishes the distillation conditions within the tower.

The catalyst is located within the tower at a location where the prevailing temperature is in the range of from about 80° C. to about 96° C. which is the required range for efficient operation of the isomerization reaction of 2MB1 and 2MB2 to 3MB1 using the aforesaid catalyst.

3MB1 formed in the isomerization reaction zone of the tower that contains the catalyst promptly rises upwardly out of the reaction zone to the top of the tower where it is removed as tower overhead and collected for further use. The remainder of the feed, including untransformed 2MB1 and 2MB2 falls downwardly to the bottom of the tower for subsequent processing as tower bottoms such as separation of 2MB1 and 2MB2 for recycle to the feed to the tower.

Reasonable variations and modifications are possible within the scope of this disclosure without departing from the spirit of this invention.

I claim:

1. A method for making alpha-olefins comprising providing a distillation tower having a top end and a bottom end, employing at least one olefin double bond isomerization catalyst bed in said tower to form an isomerization reaction zone in said tower, introducing into said tower above said catalyst bed a feed material containing at least one olefin having an internal double bond and at least one alpha-olefin so that said at least one alpha olefin already in said feed migrates upwardly to said top end for removal from said tower while said at least one internal double bond olefin falls into contacts with said catalyst, transforming in contact with said catalyst at least part of said internal double bond olefin to an alpha-olefin, establishing distillation conditions in said tower that favor said isomerization reaction where said catalyst bed is disposed in said tower and which favor the removal of alpha-olefin from said catalyst bed to said top end of said tower, whereby alpha-olefin as formed in said catalyst bed is promptly removed from said catalyst bed to said top end of said tower for removal from said tower and unreacted internal double bond olefins exit said catalyst bed at said bottom end of said tower, said isomerization reaction cannot reach its natural equilibrium between relative amounts of internal olefin and alpha-olefin in said reaction zone, and reboiling unreacted internal double bond olefins that exit said catalyst bed at said bottom end of said tower up into said isomerization reaction zone.

2. The method of claim 1 wherein said feed is a hydrocarbon containing stream that contains at least in part olefins having from 4 to 12 carbon atoms per molecule, inclusive, said olefins comprising a mixture of internal olefins and alpha-olefins.

3. The method of claim 2 wherein said mixture contains olefins having from 4 to 10 carbon atoms per molecule, inclusive, and has at least 5 weight percent internal olefins based on the total weight of said feed.

4. The method of claim 1 wherein said isomerization catalyst bed contains at least one catalyst selected from the group consisting of acidic ion exchange resins, per fluorinated polymer sulfonic acids, phosphoric acid catalyst, carboxylic acid catalyst, fluorinated alkyl sulfonic acid catalyst, alumina alkali metal, zinc aluminate, zirconia, sulfated zirconia, cobalt sulfur catalyst, ruthenium oxide, alumino phosphate, and zeolite.

5. The method of claim 1 wherein said distillation conditions establish a temperature of from about 0° C. to about 500° C. in said catalyst bed and a pressure range in said tower and catalyst bed that favors alpha-olefins rising to the top end of said tower and internal olefins falling to the bottom end of said tower.

* * * * *